United States Patent [19]

Warolin et al.

[11] 4,129,660

[45] Dec. 12, 1978

[54] DERIVATIVES OF CIS-EPOXY-1,2-PROPYL-PHOSPHONIC ACID AND DRUGS CONTAINING IN PARTICULAR AS ACTIVE INGREDIENTS DERIVATIVES OF CIS-EPOXY-1,2-PROPYLPHOSPHONIC ACID IN DEXTROROTATORY FORM

[75] Inventors: Christian J. Warolin, Paris; Pierre Chabrier de Lassauniere, La Chesnaye; Nguyen T. Thuong, La Cellerie, all of France

[73] Assignee: Agence Nationale de Valorisation de la Recherche (ANVAR), Paris, France

[21] Appl. No.: 801,921

[22] Filed: May 31, 1977

Related U.S. Application Data

[62] Division of Ser. No. 704,629, Jul. 12, 1976.

[30] Foreign Application Priority Data

| | | | |
|---|---|---|---|
| Jul. 16, 1975 | [GB] | United Kingdom | 29918 |
| Jul. 16, 1975 | [GB] | United Kingdom | 29919 |

[51] Int. Cl.[2] .......... A61K 31/665
[52] U.S. Cl. .......... 424/203
[58] Field of Search .......... 424/203

[56] References Cited

U.S. PATENT DOCUMENTS

| | | | |
|---|---|---|---|
| 3,637,766 | 1/1972 | Glamkowski et al. | 424/203 |
| 3,679,711 | 7/1972 | Firestowe | 424/203 |

OTHER PUBLICATIONS

Chemical Abstracts 72:67107W (1970).

*Primary Examiner*—Jerome D. Goldberg
*Attorney, Agent, or Firm*—Bacon & Thomas

[57] ABSTRACT

New asymmetrical derivatives of cis-epoxy-1,2-propylphosphonic acid, corresponding to the formula:

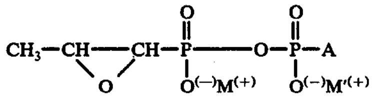

(I)

in which:

$M^{(+)}$ and $M'^{(+)}$, which are identical or different, are chosen from the hydrogen ion and the inorganic or organic cations, A is chosen from:

the straight or branched alkyl and alkoxy radicals having 1 to 8 carbon atoms and being able to comprise at least one substitutent constituted by an epoxy bridge or chosen from the alkoxy radicals having 1 to 5 carbon atoms, alkoxycarbonyl whose alkyl radical comprises from 1 to 5 carbon atoms, amino, alkylamino, nitrile, the aryl, aralkyl, arylkoxy radicals which are substituted or not, said products being useful particularly as drugs.

4 Claims, No Drawings

DERIVATIVES OF CIS-EPOXY-1,2-PROPYL-PHOSPHONIC ACID AND DRUGS CONTAINING IN PARTICULAR AS ACTIVE INGREDIENTS DERIVATIVES OF CIS-EPOXY-1,2-PROPYLPHOSPHONIC ACID IN DEXTROROTATORY FORM

This is a division of application Ser. No. 704,629, filed July 12, 1976.

This invention relates to cis-1,2-epoxypropyl-pyrophosphonic acid derivatives, their preparation and their pharmaceutical use.

Cis-1,2-epoxypropyl-phosphonic acid and a number of its derivatives are well known, see in this respect French Patent Specifications Nos. 69 15920 and 69 30750 as well as the specifications of French Patent Applications Nos. 70 02084 and 70 02085, the specification of German Patent Application No. 1046047 and U.S. patent specification No. 2,770,610.

According to the present invention, there are provided asymmetric compounds of the formula I

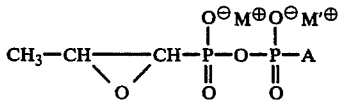
(I)

wherein $M^{(+)}$ and $M'^{(+)}$ which are the same or not, represent a hydrogen ion or an inorganic or organic cation.

A is chosen among straight or branched alkyl or alkyl group having 1 to 8 carbon atoms and being unsubstituted or substituted by at least an epoxy bridge or an alkoxy radical having 1 to 5 carbon atoms in the alkyl radical, an amino group, an alkylamino group, or a nitrile group.

aryle, aralkyle or aryloxy radical unsubstituted or substituted.

the $M^{(+)}$ and $M'^{(+)}$ groups may together form a divalent cation, for example an alkaline earth metal cation; further, when A group has an amino group, this group may be an ammonium group and, in this case, this group may constitute the cation $M^{(+)}$.

The compounds of formula I exist in optical isomer form. The present invention includes the individual optical isomers and racemic mixtures of the compounds of formula I.

The compounds of formula I may be prepared by epoxidation of a compound of the formula II:

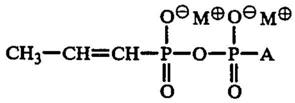
(II)

(wherein A and $M^{\oplus}$ are as defined above). In addition, when in the desired product of formula I A represents an epoxy-substituted alkyl group, the compound of formula I may be prepared by epoxidation of a corresponding compound of formula II wherein A represents an alkenyl group, which alkenyl group is epoxidized with the prophenyl group attached to the other phosphorus atom.

The epoxidation of the compound of formula II can be carried out by any appropriate method, for example by the action of oxygenated water in the presence of a catalyst such as oxodiperoxoaquohexamethylphosphoramido tungsten $[W(O_2)O]$ . HMPT. $H_2O$ or the tungstate of benzyltrimethylammonium hydroxyde (Triton B) or sodium tungstate and disodium edetate (titriplex III) for example.

The starting compounds of formula II are novel. Accordingly the invention also provides compounds of formula II defined above.

The compounds of formula II may themselves be prepared by reaction of a compound of the formula III:

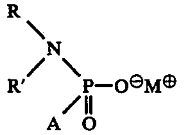
(III)

wherein

A is as defined above (including alkenyl), each of R and R', which may be the same or different, represents a hydrogen atom or an alkyl group having 1 to 4 carbon atoms, and $M^{\oplus}$ is an ammonium, for example $^{\oplus}N(CH_3)_4$, $H_2N^{\oplus}(CH_3)_2$, cation or a metallic, for example $Na^{\oplus}$, cation) with cis-1-propenylphosphonic acid of the formula:

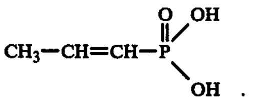

The reaction between the compound of formula III and the propenylphosphonic acid may be carried out at a temperature of 20°-100° C. in an organic solvent for example, acetone, acetonitrile, alcohols, nitromethane, dimethylformamide, dimethylsulphoxide or hexamethylphosphorotriamide.

The compounds of formula III may be prepared by reaction of a tertiary amine, for example trimethylamine, or a metal cyanide or iodide, for example sodium cyanide or iodide, with a methyl ester of the formula IV:

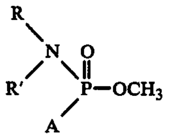
(IV)

(wherein A, R and R' are as defined above) in an organic solvent e.g. acetone, acetonitrile, nitromethane; dimethylformamide or dimethylsulphoxide. Compounds of formula III, which are only slightly soluble in the solvent used, may be isolated by simple filtration.

Quaternary ammonium salts of formula III may readily be obtained in the pure state. Preferably compounds wherein both R and R' represent methyl groups are prepared.

The compounds of formula III may also be prepared by reaction of a primary or secondary amine with an anhydride of the formula V:

$$(APO)_n \qquad (V)$$

wherein A is as defined above and n is 1, 2 or 3.

Metal salts of compounds of formula II may be prepared from mixed quaternary ammonium and amine salts for example either by exchange on an Amberlite resin IR 120(M⊕), by double decomposition with sodium salicylate in alcoholic medium or with calcium chloride in alcoholic medium.

Further, when the radical A comprises an amine substituent which is an ammonio radical (A is then of the form

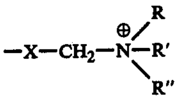

wherein X is an alkyleneoxy radical and R, R' and R'' are alkyl radicals or hydrogen atoms), the process of preparation may be carried out according to the following scheme:

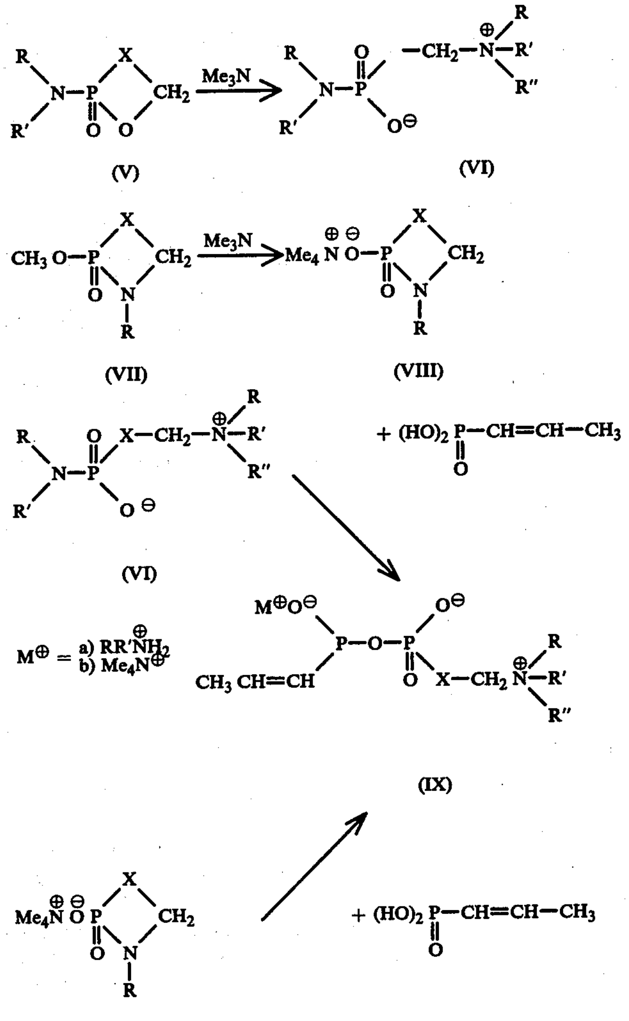

1) (V) (VI)

or 2) (VII) (VIII)

3a) (VI)

or M⊕ = a) RR'NH2⊕ b) Me4N⊕

(IX)

3b) (VIII)

(Wherein Me represents a methyl group).

The epoxidation of the compound of formula IX then leads to a compound of the formula I*a:*

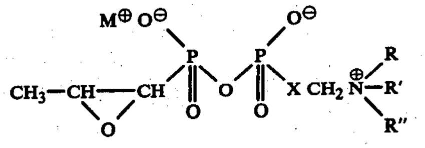

(Ia).

The compounds of formula I have been found to possess antibilharziennic and antibiotic properties. Accordingly the invention also provides a pharmaceutical composition, particularly an antibilharziasis medicament or an antibiotic drug, which comprises a compound of formula I together with a pharmaceutically acceptable carrier or diluent.

The invention also provides a treatment of a patient which comprises administration to the patient of a compound of formula I.

The present invention is further illustrated in the following Examples. In the Examples the products were obtained as racemic mixtures.

EXAMPLE 1

Sodium $P^1$-methyl, $P^2$-(±) cis-1,2-epoxypropylpyrophosphonate (SAB 74 202)

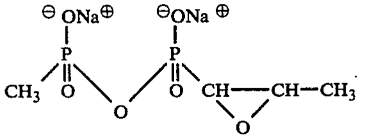

(a) O-Methyl-methylphosphonic acid chloride

To a solution of 208.5 parts $PCl_5$ in 1600 parts $CCl_4$ there is added at 70° C. in small portions and with stirring 183 parts tetramethylammonium methyl-methylphosphonate (M.Pt. = 195° C. Bull. Soc. Chim. 1965. page 1925). After the addition stirring is continued for 3 hours at the same temperature. The tetramethylammonium hydrochloride is filtered off, the solvent removed and the product purified by distillation.

B.Pt.$_{12}$ = 62° C.
$n_D^{20}$ = 1.4360
Yield = 85%

(b) Methyl dimethylamido-methylphosphonate

To a solution of 101 parts triethylamine and 48 parts dimethylamine in 250 parts benzene, there is added at 0° C. and with stirring a solution of 128.5 parts O-methyl-methylphosphonic acid chloride and 50 parts benzene.

The addition ended, stirring is continued for 3 hours at ambient temperature. The mixture is filtered, the solvent removed and the product then purified by distillation.

Boiling Point $_2$ = 51° C.
$n_D^{20}$ = 1.436
Yield ≃ 90%

(c) Tetramethylammonium dimethylamido-methylphosphonate

There is allowed to react for several days at 80°-90° C. and in a sealed reactor which can support pressure, a solution of 68.5 parts methyl dimethylamido-methylphosphonate and 59 parts trimethylamine in 180 parts acetonitrile. The tetramethylammonium salt formed is separated by filtration after having been cooled to 0° C. 78.4 parts of a white solid, very soluble in water and alcohol and soluble in hot nitromethane, are obtained.

M.Pt. = 232°-233° C.
Yield = 80%

(d) Tetramethylammonium dimethylammonium $P^1$-methyl, $P^2$-cis-1-propenyl-pyrophosphonate There is stirred overnight at 60° C. a mixture of 19.6 parts tetramethylammonium dimethylamido-methylphosphonate, 12.2 parts cis-1-propenylphosphonic acid and 100 parts acetonitrile. The insolubles are filtered off, the solvent evaporated in vacuo and 25 parts of a white solid obtained the NMR specrum of which indicated the following formula

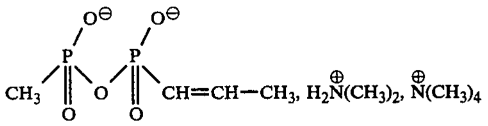

Yield = 78.5%

(e) Sodium $P^1$-methyl, $P^2$-cis-1-propenyl-pyrophosphonate

The 25 parts of the compound prepared as above are dissolved in a little water and the aqueous solution passed over a column of Amberlite resin IR 120 ($Na^+$). The water is evaporated off in vacuo and the solid obtained taken up in hot isopropanol, filtered, dried and a white solid, readily soluble in water, slightly soluble in alcohol and insoluble in organic solvents, obtained.

M.Pt. > 250° C.
Yield ≃ 95%

| Elementary analysis $C_4H_8O_5P_2Na_2$ | C | H | P |
|---|---|---|---|
| Calculated | 19.4 | 3.26 | 25.4 |
| Found | 19.29 | 3.57 | 25.18 |
| NMR (H) $D_2O$ | 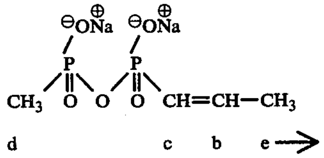 | | |

a (m) δ = 1.85 ppm
b, c (m) δ ~ 5 to 7 ppm
d (d) δ = 1.3 ppm, τ = 16.7 Hz
TLC Silica gel (type 60)
Eluant $CH_3OH$ = 80; $Et_3H$ = 5; $H_2O$ = 10
Rf = 0.66

(f) Sodium $P^1$-methyl, $P^2$-(±) cis-1,2-epoxypropylpyrophosphonate

There is stirred overnight a mixture of 12.2 parts of sodium $P^1$-methyl, $P^2$-cis-1-propenyl-pyrophosphonate, 22 parts of 110 volume oxygenated water, 0.08 parts titriplex II and 0.24 parts sodium tungstate. The epoxidised compound is precipitated with acetone and filtered. The solid obtained is dissolved in a water/alcohol (60:40) mixture and passed over a column of neutral alumina (eluant: water/alcohol 60:40), the solvent evaporated off and 7.4 parts of a white solid, readily soluble in water (pH~7), are obtained.

M.Pt. > 250° C.
Yield = 57%

| Elementary analysis $C_4H_8O_6P_2Na_2$ | C | H | P | Na |
|---|---|---|---|---|
| Calculated | 18.45 | 3.08 | 23.85 | 17.7 |
| Found | 18.06 | 3.12 | 23.42 | 16.9 |
| NMR (H)$D_2O$ | 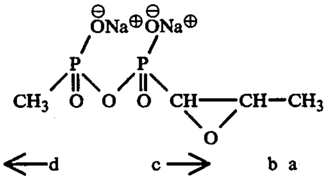 | | | |

a (d) δ = 1.45 ppm, τ = 6 Hz
b, c (m) δ ~ 2.90 and 3.32 ppm
d (d) δ = 1.4 ppm, τ = 16.7 Hz
TLC Silica gel G (type 60)
Eluant $CH_3OH$: 80, $Et_3N$: 5, $H_2O$: 10
Rf = 0.654

EXAMPLE 2

Sodium $P^1$-phenyl, $P^2$-(±)cis-1,2-epoxypropylpyrophosphonate (SAB 74 200).

(a) Methyl phenyl-phosphonite

To a solution of 64 parts anhydrous methanol in 250 parts benzene there is added slowly at 0°-5° C. with stirring under a nitrogen atmosphere and under a slight subatmospheric pressure 179 parts phenylphosphonic acid dichloride.

When the addition is ended, stirring is continued for 3 hours at ambient temperature; the solvent is removed and the product then purified by distillation.

B.Pt.$_{0.05}$ = 104° C.
Yield = 65%

(b) Methyl dimethylamido-phenylphosphonate.

To a solution of 78 parts methyl phenyl-phosphonite in 200 parts $CCl_4$ there is added slowly with stirring at 0°-5° C. 48 parts dimethylamine.

After the addition, stirring is continued for several hours and the reaction mixture left at ambient temperature overnight. It is filtered, the filtrate washed with a bicarbonate solution, the solvent eliminated and the product then separated by distillation.

B.Pt.$_{0.5}$ = 105° C.
Yield = 70%

(cα) Tetramethylammonium dimethylamido-phenylphosphonate.

Operating as in Example 1c) but using 99.5 parts methyl dimethylamido-phenylphosphonate, 111 parts of a white solid are obtained.

M.Pt. = 245° C.
Yield = 86%

(cβ) Sodium dimethylamido-phenylphosphonate.

There is introduced, into a reaction vessel provided with a distillation column, a mixture of 19.5 parts phenylphosphonic acid dichloride and 10.2 parts acetic anhydride. The reaction mixture is heated with stirring to 110° C. with distillation of the acetylchloride formed. After 1 hour 30 minutes reaction, the volatile compounds are eliminated in vacuo and the residue then taken up in acetonitrile.

To the solution there is added slowly at about 0° C. 30 parts of a solution of 40% dimethylamine in acetonitrile. The reactor was then sealed hermetically and heated overnight at 60° C.

The solvent is evaporated off, the residue taken up in a little water and then the aqueous solution passed over an Amberlite IR 120 ($NA^+$) resin column.

17 parts of sodium dimethylamido-phenylphosphonate are obtained in the form of a white solid.

Yield = 85%

(d) Sodium $P^1$-phenyl, $P^2$-cis-1-propenyl-pyrophosphonate

There is stirred overnight at 55° C. a mixture of 27 parts of tetramethylammonium dimethylamido-phenylphosphonate, 12.2 parts cis-1-propenylphosphonic acid and 200 parts acetonitrile. The mixture is filtered, the solvent evaporated and the white solid obtained as residue.

The solid is taken up in a little water, and the aqueous solution passed over a column of Amberlite resin IR 120 ($Na^+$) and the operation concluded as in Example 1(e).

29.16 parts of a white solid, which is very soluble in water, slightly soluble in alcohol and insoluble in organic solvents, are obtained.

M.Pt. > 250° C.
Yield = 90%

| Analysis $C_9H_{10}P_2O_5Na_2 . H_2O$ | C | H | P |
|---|---|---|---|
| Calculated | 33.4 | 3.70 | 29.15 |
| Found | 33.77 | 3.51 | 19.24 |
| NMR (H) $D_2O$ | | | |

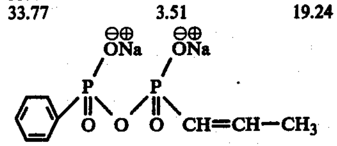

d c b a a (m) δ = 1.85 ppm
b, c (m) δ ~ 5 to 7 ppm
d (m) δ = 7.6 ppm
TLC Silica gel G (type 60)
Eluant $CH_3OH$: 80; $Et_3N$: 5; $H_2O$: 15
Rf = 0.698

(e) Sodium $P^1$-phenyl, $P^2$-(±) cis-1,2-epoxypropylpyrophosphonate

There is stirred overnight at ambient temperature a mixture of 3 parts sodium $P^1$-phenyl, $P^2$-cis-1-propenyl-pyrophosphonate, 1.6 parts of 110 volume oxygenated water, 0.01 parts titriplex III and 0.03 parts sodium tungstate. The operation is concluded as in Example 1f) using a water/alcohol solution (60:40).

1.76 parts (yield 56%) of a white solid, (M.Pt. > 250° C.) which is very soluble in water (pH~6.5), slightly soluble in alcohol and insoluble in organic solvents, are obtained.

| Analysis $C_9H_{10}O_6P_2Na_2 . H_2O$ | C | H | P | Na |
|---|---|---|---|---|
| Calculated | 31.76 | 3.53 | 18.23 | 13.52 |
| Found | 31.52 | 3.55 | 18.13 | 12.8 |
| NMR (H) $D_2O$ | | | | |

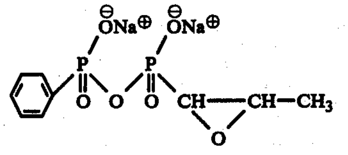

d c b a a (d) δ = 1.32 ppm, τ = 6 Hz
b,c, (m) δ ~ 2.70-3.12 ppm
d (m) δ = 7.60 ppm
TLC Silica gel (type 60)
Eluant $CH_3OH$: 80, $Et_3N$: 5; $H_2O$: 15
Rf = 0.683

EXAMPLE 3

Sodium $P^1$-2,3-epoxypropyl, $P^2$-(±) cis-1,2-epoxypropylpyrophosphonate (SAB 74 204).

(a) O-methyl-allylphosphonic acid chloride

To a solution of 208.5 parts $PCl_5$ in 1600 parts $CCl_4$, there is added at 70° C. in small portions and with stirring 220 parts of tetramethylammonium methyl-allylphosphonate (M.Pt. = 174° C., Bull. Soc. Chim., 1965, page 1925).

After the addition, stirring is continued for 1 hour at 70° C., the mixture filtered, the solvent removed and the product purified by distillation.

B.Pt.$_{15}$ = 90°-91° C.

$n_D^{20}$ = 1.459

Yield = 78%

(b) Methyl dimethylamido-allylphosphonate.

Using 154.5 parts O-methyl-allylphosphonic acid chloride and operating according to Example 1(b) the product is obtained with quantitative yield.

B.Pt.$_{0.1}$ = 56° C.

$n_D^{20}$ = 1.4554

(c) Tetramethylammonium dimethylamido-allylphosphonate.

Operating as in Example 1(c) and using 81.5 parts methyl dimethylamido-allylphosphonate, there is obtained 89.5 parts of a white solid which is very soluble in water and alcohol.

M.Pt. = 180° C.

Yield = 81%

(d) Tetramethylammonium dimethylammonium $P^1$-allyl, $P^2$-cis-1-propenyl-pyrophosphonate.

There is stirred overnight at 60° C. a mixture of 22.2 parts tetramethylammonium dimethylamido-allylphosphonate 12.2 parts cis-1-propenylphosphonic acid and 100 parts acetonitrile. The mixture is filtered, the solvent evaporated and 30.96 parts of a white solid obtained, the NMR (H) spectrum of which indicated the following formula

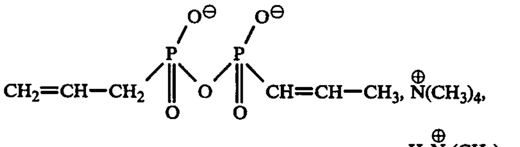

Yield = 90%

(e) Sodium $P^1$-allyl, $P^2$-cis-1-propenyl-pyrophosphonate.

Operating as in Example 1(e), the sodium salt is obtained in the form of a white solid which is very soluble in water (pH∼5)

Yield = 84%

| Analysis $C_6H_{10}P_2O_5Na_2\,H_2O$ | C | H | P | Na |
|---|---|---|---|---|
| Calculated | 25 | 4.16 | 21.5 | 15.9 |
| Found | 25.06 | 3.98 | 21.95 | 15.84 |

NMR (H) $D_2O$

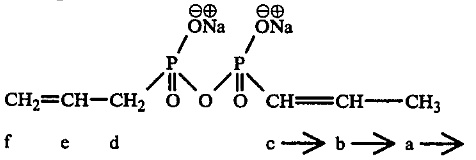

a (m) δ = 1.88 ppm b,c (m) δ ∼ 5 to 7 ppm d (dd) δ = 2.48 and 2.60 ppm e, f (m) δ ∼ 4.9 and 6 ppm TLC Silica gel (type 60)

Eluant $CH_3OH$: 80; $Et_3N$: 5; $H_2O$: 10

Rf = 0.676

(f) Sodium $P^1$-2,3-epoxypropyl, $P^2$-(±)-cis-1,2-epoxypropylpyrophosphonate.

There is stirred overnight at ambient temperature a mixture of 2.88 parts of sodium $P^1$-allyl, $P^2$-cis-1-propenylpyrophosphonate, 7 parts of 110 volume oxygenated water and 0.03 parts titriplex III, and 0.08 parts sodium tungstate. The operation is concluded as in Example 1(f).

2.17 parts of a white solid, very soluble in water (pH∼ are obtained.

Yield = 66%

| Analysis $C_6H_{10}P_2O_7Na_2 \cdot 1.5\ H_2O$ | C | H | P | Na |
|---|---|---|---|---|
| Calculated | 21.8 | 3.9 | 18.8 | 13.98 |
| Found | 22.9 | 4.2 | 18.9 | 14.14 |

NMR (H) $D_2O$

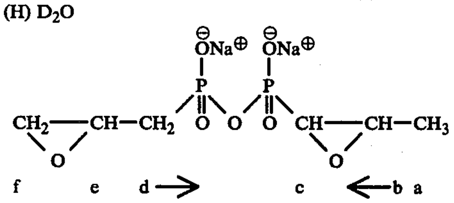

a (d) δ = 1.76 ppm, τ = 5.7 Hz b,c,d,e,f, (m) δ between 1.8 and 3.5 ppm

TLC Silica gel (type 60)

Eluant $CH_3OH$: 80; $Et_3N$: 5; $H_2O$: 10

Rf = 0.571

EXAMPLE 4

Sodium $P^1$-benzyl, $P^2$ (±) cis-1,2-epoxypropylpyrophosphonate (SAB 74 210).

(a) Tetramethylammonium dimethylamido-benzylphosphonate

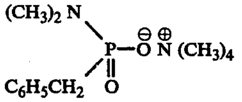

There is stirred for 5 hours at 50° C. a mixture of 100 parts dimethyl benzylphosphonate and 104 parts $PCl_5$ in 120 parts $CCl_4$.

The solvent and $POCl_3$ are removed in vacuo and the residue obtained then slowly added at around 0° C. and with stirring to a solution of 25 parts dimethylamine and 51 parts triethylamine in 100 parts benzene. The solids are removed by filtration and the solvent removed in vacuo.

The oily residue obtained is then treated with 60 parts trimethylamine in acetonitrile according to Example 1(c). 90 parts of a white hygroscopic solid are obtained.

M.Pt. = 190° C.

Yield = 66%

(b) Sodium $P^1$-benzyl, $P^2$-cis-1-propenyl-pyrophosphonate.

There is stirred overnight at 65° C. a mixture of 27.2 parts tetramethylammonium dimethylamido-benzylphosphonate, 12.2 parts cis-1-propenylphosphonic acid and 100 parts acetonitrile. The mixture is filtered, the solvent evaporated and the residue then taken up in a little water.

The aqueous solution is passed over a column of Amberlite IR 120 ($Na^+$) resin, the water evaporated off in vacuo, the residue taken up in acetone; a white precipitate, which is separated by filtration, is obtained.

Yield = 75%

| Elementary analysis : $C_{10}H_{12}O_5Na_2P_2 . H_2O$ | C | H | P |
|---|---|---|---|
| Calculated | 35.5 | 4.15 | 18.4 |
| Found | 35.43 | 4.14 | 18.43 |

NMR (H) $D_2O$

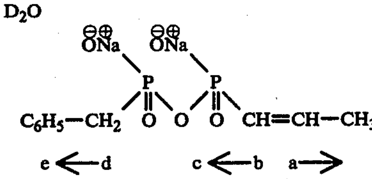

a (m) δ ~ 1.9 ppm
b,c (m) δ between 5.3 and 7 ppm
d (2d) δ = 3.1 and 3.15 ppm, τ = 20 Hz
e (s) δ = 7.3 ppm
TLC Silica gel G (type 60)
Eluant $CH_3OH$ = 80; $Et_3N$ = 5; $H_2O$ = 10
Rf = 0.78

(cα) Sodium $P^1$-benzyl, $P^2$-(±) cis-1,2-epoxypropylpyrophosphonate.

There is stirred overnight at ambient temperature a mixture of 3.2 parts sodium $P^1$-benzyl, $P^2$-cis-1-propenylpyrophosphonate, 7 parts of 110 volume oxygenated water, 0.05 parts sodium tungstate and 0.02 parts titriplex III; the product formed is precipitated with acetone and separated by filtration. The compound is then purified by passing over a column of activated alumina (eluant: water/methanol = 4:1). The solvent is evaporated off in vacuo and the white solid obtained dried over $P_2O_5$.

Yield = 48%.

| Elementary analysis : $C_{10}H_{12}O_6Na_2P_2 . 2H_2O$ | C | H | Na | P |
|---|---|---|---|---|
| Calculated | 32.25 | 4.3 | 12.37 | 16.66 |
| Found | 32.31 | 4.27 | 12.74 | 16.32 |

NMR (H) $D_2O$

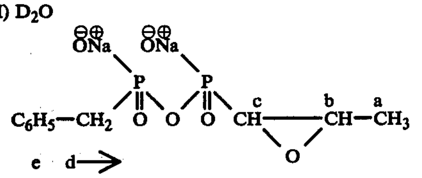

a (d) δ = 1.45 ppm, τ=5.3 Hz
b, c, d (m) δ between 2.8 and 3.4
e (s) δ = 7.4 ppm
TLC Silica gel G
Eluant $CH_3OH$: 80; $Et_3N$: 5; $H_2O$: 10
Rf: 0.79

(c β) Sodium $P^1$-benzyl, $P^2$-(±) cis-1,2-epoxypropylpyrophosphonate.

There is stirred for 24 hours at ambient temperature a mixture of 2 parts sodium $P^1$-benzyl, $P^2$ cis-1-propenylpyrophosphonate, 0.25 parts of 85% oxygenated water, 0.06 parts [W $(O_2)_2O$]. HMPT. $H_2O$ and 9 parts methanol. 20 parts acetone are then added to the reaction medium, the precipitate filtered off and 1.6 parts of a white solid, having the same characteristics as the compound prepared under 4cα), obtained.

EXAMPLE 5

Sodium $P^1$-methoxycarbonylmethyl, $P^2$-(±) cis-1,2-epoxypropylpyrophosphonate (SAB 74212)

(a) Tetramethylammonium dimethylamido-methoxycarbonylmethyl-phosphonate.

There is stirred for 1 day at ambient temperature a mixture of 104.25 parts phosphorus pentachloride, and 120.5 parts tetramethylammonium methyl-methoxycarbonylmethylphosphonate in 160 parts $CCl_4$.

The solids are separated by filtration, the solvent and $POCl_2$ removed in vacuo and the preparation then concluded as in Example 4(a) to give 55.6 parts of a white solid.

M.Pt. = 123° C.
Yield = 57%

(b) Sodium $P^1$-methoxycarbonylmethyl, $P^2$-cis-1-propenylpyrophosphonate.

Operating as in Example 4(b) and reacting 5.08 parts tetramethylammonium dimethylamido-methoxycarbonylmethylphosphonate, 2.44 parts cis-1-propenylphosphonic acid and 20 parts acetonitrile, 4.95 parts (yield 82%) of a white solid are obtained.

NMR (H) $D_2O$

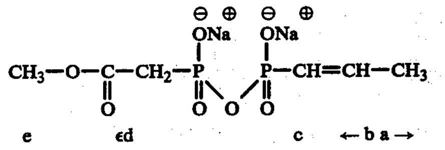

a (m) δ = 1.88 ppm
b, c (m) δ between 5.2 and 7 ppm
d (m) δ between 2.74 and 3.10 ppm
e (s) δ = 3.68 ppm.

(c) Sodium $P^1$-methoxycarbonylmethyl, $P^2$-(±) cis-1,2-epoxypropylpyrophosphonate.

There is reacted at ambient temperature for 1 hour with stirring a mixture of 4 parts of the compound prepared earlier under 5(b), 6 parts of 110 volume oxygenated water, 0.06 parts of $Na_2WO_4$ and 0.02 parts titriplex III. The product formed is precipitated with acetone and separated by filtration. 4 parts of a white solid, which are purified by chromatography on activated alumina, are obtained.

| Analysis: $C_6H_{10}O_8Na_2P$ | C | H | P | Na |
|---|---|---|---|---|
| Calculated | 22.62 | 3.14 | 19.5 | 14.45 |
| Found | 22.14 | 3.32 | 18.72 | 14.62 |

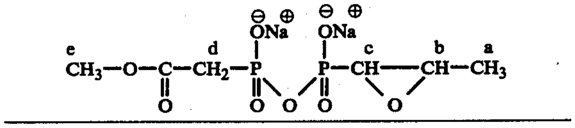

a (d) δ = 1.52 ppm, τ = 5.13 Hz
b,c,d, (m) δ ~ 3.1 ppm
e (s) δ = 3.78 ppm
TLC Silica gel (type 60)
Eluant: MeOH: 80; $Et_3N$: 5; $H_2O$: 5
Rf: 0.65

EXAMPLE 6

Calcium salt of $P^2$-methyl-phosphoric, $P^2$-(∓)cis-1, 2-epoxy -propylphosphonic acid anhydride (SAB 73 196).

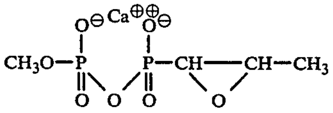

(a) Calcium salt of $P^1$-methyl-phosphoric, $P^2$-cis-1-propenylphosphonic acid anhydride.

There is introduced into a reaction vessel 21.2 parts by weight tetramethylammonium methyl-dimethylamidophosphate (C.R. Acad. Sci. 1959, 249, 1240), 12.2 parts by weight cis-1-propenylphosphonic acid (J. Org. Chem. 1970, 35, 3510) and 80 parts by weight acetonitrile.

The reaction mixture becomes homogeneous after several hours stirring at 55° C. and with the exclusion of humidity. Stirring is then continued overnight at the same temperature, the small quantity of precipitate formed is removed by filtration and the acetonitrile is evaporated off in vacuo. To this residue, dissolved in a minimum amount of a mixture of 2 parts by volume ethanol and 1 part by volume water, there is added, at ambient temperature and with stirring, a concentrated solution of calcium chloride in the same alcohol - water mixture. The precipitate formed is filtered off, taken up in hot methanol and then dried in vacuo over $P_2O_5$.

22.6 parts (yield 79%) of a white solid, soluble in water (pH ~ 5) and insoluble in organic solvents, is obtained.

Melting point: > 300° C.

Elementary analysis shows that the product crystallises with one molecule of water.

| Analysis $C_4H_8O_6P_2Ca \cdot H_2O$ | C | H | P | Ca |
|---|---|---|---|---|
| Calculated | 17.64 | 3.67 | 22.79 | 14.7 |
| Found | 17.56 | 3.54 | 22.95 | 14 |

NMR(H) : $D_2O$

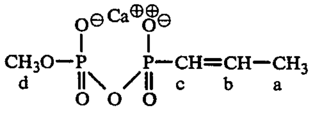

a (m) δ = 1.90 ppm
b, c (m) δ ~ 5 to 7 ppm
d (d) δ = 3.6 ppm, τ = 10.6 Hz
TLC Silica gel G (type 60)
Eluant: $CH_3OH$: 80, $NEt_3$: 5, $H_2O$: 20
Rf = 0.73

(b) Calcium salt of $P^1$-methylphosphoric, $P^2$-(±) cis-1,2-epoxypropylphosphonic acid anhydride.

A mixture of 14.4 parts of the calcium salt of $P^1$-methylphosphoric, $P^2$-bis-1-propenylphosphonic acid anhydride, 20 parts of 110 volume oxygenated water, 0.28 parts sodium tungstate and 0.08 parts titriplex III is stirred overnight at ambient temperature. The epoxidised compound is precipitated with acetone, isolated by filtration and then purified in the following manner: the solid obtained is dissolved in the minimum of water, the pH of the solution is adjusted to 8.5 with calcium hydroxide solution, the precipitate is removed by filtration, the filtrate is concentrated in vacuo and then ethanol is added with stirring to this solution until a slight precipitate is formed, which precipitate is removed by filtration; the product is then precipitated with acetone, filtered off and dried under vacuum over $P_2O_5$. 8.35 parts of a white solid, soluble in water (pH ~ 5) and insoluble in organic solvents, are obtained.

Melting point: > 300° C.
Yield = 58%

| Elementary analysis $C_4H_8O_7P_2Ca \cdot H_2O$ | C | H | P | Ca |
|---|---|---|---|---|
| Calculated | 16.65 | 3.47 | 21.7 | 13.88 |
| Found | 17.47 | 3.86 | 20.91 | 13.85 |

NMR (H) : $D_2O$.

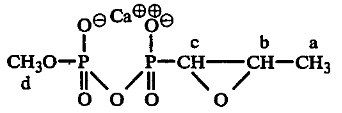

a (d) δ = 1.5 ppm, τ = 6 Hz
b, c (m) δ ~ 2.9 to 3.4 ppm
d (d) δ = 3.65, τ = 10.6 Hz
TLC Silica gel G (type 60)
Eluant $CH_3OH$: 80, $Et_3N$: 5; $H_2O$: 20
Rf = 0.85

EXAMPLE 7

Disodium salt of $P^1$-methylphosphoric, $P^2$-(∓) cis-1,2-epoxy-propylphosphonic acid anhydride (SAB 74 207)

(aα) Disodium salt of $P^1$-methylphosphoric, $P^2$-cis-1-propenylphosphonic acid anhydride.

There is reacted with stirring overnight at 55° C. a mixture of 21.2 parts tetramethylammonium methyl-dimethylamidophosphate, 12.2 parts by weight cis-1-propenylphosphonic acid and 80 parts acetonitrile. The insolubles are removed by filtration, the solvent evaporated off and the residue taken up in a little water and then the aqueous solution passed over a column of Amberlite resin IR 120 (Na+). The water is evaporated off in vacuo, the residue taken up in hot isopropanol, filtered, dried and 20 parts of a white solid are thus obtained. NMR (H): $D_2O$

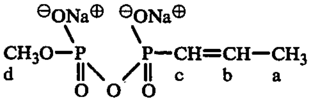

a (m) δ = 1.85 ppm
b, c (m) δ ~ 5.5 to 7 ppm
d (d) δ = 3.57 ppm, τ = 11.3 Hz
TLC Silica gel G type 60
Eluant $CH_3OH$: 80, $NEt_3$: 5, $H_2O$: 5
Rf: 0.671

(aβ) Disodium salt of $P^1$-methylphosphoric, $P^2$-cis-1-propenylphosphonic acid anhydride.

(i) Sodium methyl-dimethylamidophosphate.

There is reacted with stirring for several hours at 60°-70° C. a mixture of 153 parts dimethyldimethylamidophosphate, 50 parts sodium cyanide and 400 parts dimethylsulphoxide (DMSO). The preparation is left overnight at ambient temperature, the product separated off by filtration, washed with DMSO and then with acetone and dried under vacuum. 140 parts of a white solid, readily soluble in water, are obtained.

(ii) Disodium salt of $P^1$-methylphosphoric, $P^2$-cis-1-propenylphosphonic acid anhydride.

There is reacted with stirring overnight at 70° C. a mixture of 16.1 parts sodium methyl-dimethylamidophosphate, 12.2 parts cis-1-propenylphosphonic acid and 60 parts acetonitrile. The solvent is evaporated off in vacuo and the residue dissolved in a minimum of methanol. To this alcoholic solution there is added with stirring and at ambient temperature a solution of 4.1 parts sodium hydroxide in methanol, and the stirring then continued for 1 hour at ambient temperature. The mixture is then brought to reflux and filtered hot, the solid is washed with alcohol and dried in vacuo. 23.4 parts of a white solid, having the same physical constants as the product prepared under (aα), was obtained.

(b) Disodium salt of $P^1$-methylphosphoric, $P^2$-(±)-cis-1,2-epoxypropylphosphonic acid anhydride.

There is stirred for 1 hour 30 minutes at ambient temperature a mixture of 5 parts of the compound obtained under (a), 0.07 parts $[(WO_2)O].HMPT.H_2O$ and 2.7 parts 50% oxygenated water.

The epoxidised compound so formed is precipitated with acetone, filtered and the product then purified by chromatography over a column of activated alumina (eluant: water/methanol 5:1). There are obtained 4.1 parts of a white solid, the physical constants of which were as follows: NMR (H) $D_2O$

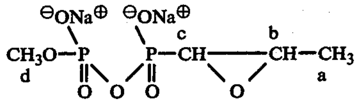

a (d) $\delta$ = 1.5 ppm, $\tau$ = 5.3 Hz
b,c (m) $\delta \sim$ 3.3 ppm
d (d) $\delta$ = 3.65 ppm, $\tau$ = 11.3 Hz
TLC Silica gel G (type 60)
Eluant $CH_3OH$: 80, $NEt_3$: 5, $H_2O$: 10
Rf = 0.525

EXAMPLE 8

Sodium salt of $P^1$-(2-trimethylammonio-ethyl)-phosphoric, $P^2$-(±) cis-1,2-epoxypropylphosphonic acid anhydride (SAB 74 214)

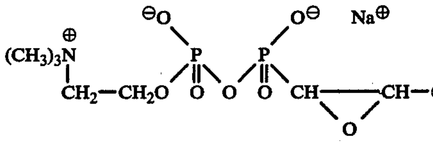

(a) Sodium salt of $P^1$-(2-trimethylammonio-ethyl)-phosphoric, $P^2$-cis-1-propenylphosphonic acid anhydride.

There is reacted overnight at 65° C. a mixture of 5.04 parts morpholino-phosphorylcholine prepared according to French Patent No. 72 43 780 of Dec. 8, 1972, 2.03 parts cis-1-propenylphosphonic acid and 20 parts acetonitrile.

The viscous residue formed is separated by decantation and then dissolved in a mixture of isopropanol and methyl cellosolve. To this solution there is added a solution of 0.5 parts alcoholic sodium hydroxide solution; the solvent is removed and the residue then taken up in acetone. A white hygroscopic precipitate is obtained which is purified by passage over activated alumina (Eluant: $H_2O/CH_3OH$:4:1).

Yield = 68%
NMR (H): $D_2O$

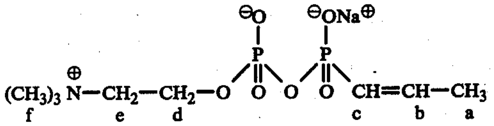

a (m) $\delta$ = 1.9 ppm
b, c (m) $\delta$ between 5.3 and 7 ppm
d (m) $\delta \sim$ 4.3 ppm
e (m) $\delta \sim$ 3.6 ppm
f (s) $\delta$ = 3.15 ppm (b) Sodium salt of $P^1$-(2-trimethylammonioethyl)-phosphoric, $P^2$-(±) cis-1,2-epoxypropylphosphonic acid anhydride.

There is stirred overnight at ambient temperature a mixture of 2.5 parts of the compound prepared under a) above, 4 parts of 110 volume oxygenated water, 0.08 parts sodium tungstate and 0.03 parts titriplex III. The epoxidised compound so formed is precipitated with acetone and then separated by filtration. 2.2 parts of a white solid, which is purified by chromatography over a column of activated alumina (eluant, water/methanol 4:1), are obtained.

| Analysis : $C_8H_{18}NO_7P_2Na$ | C | N | Na |
|---|---|---|---|
| Calculated | 29.6 | 4.32 | 7.07 |
| Found | 29.75 | 4.33 | 7.04 |

NMR (H) $D_2O$

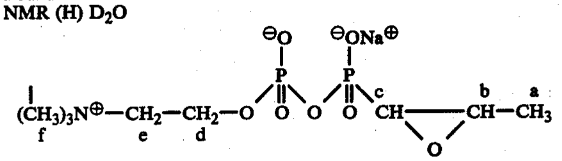

a (d) $\delta$ = 1.42 ppm $\tau$ = 5.3 Hz
b,c (m) $\delta$ between 2.6 and 3.2 ppm
d (m) $\delta$ = 4.3 ppm
e (m) $\delta$ = 3.6 ppm
f (s) $\delta$ = 3.15 ppm

EXAMPLE 9

Sodium salt of $P^1$-($\gamma$-N-isopropylammmoniopropyl)-phosphoric, $P^2$-(±)-cis-1,2-epoxypropylphosphonic acid anhydride (SAB 74 217).

(a) 2-[$(CH_3)_4N^{\oplus}$ $\ominus$]-2-oxo-3-isopropyl-1,3,2-oxazaphosphorinane.

To a solution of 13.95 parts 2-chloro-1,3,2-dioxaphosphorinane in $CCl_4$ there is added slowly at 0° C. 16 parts dry bromine. After dilution of the reaction medium with diethyl ether there is added slowly at −20° C. a mixture of 3.2 parts methanol and 10.1 parts triethylamine and then at ambient temperature a mixture of 5.9 parts isopropylamine and 10.1 parts triethylamine. The reaction medium is washed with water, dried and then evaporated.

The residue dissolved in tetrahydrofuran is treated at ambient temperature with 2.7 parts sodium hydride; after hydrogen evolution has ceased, stirring is continued for 2 hours at 50° C.

After recooling, the excess sodium hydride is destroyed by adding water, the reaction medium neutralised with dilute HCl, and the 2-methoxy-2-oxo-3-isopropyl-1,3,2-oxazaphosphorinane extracted with chloroform and then purified by distillation (B.Pt. $_{0.05}$ 85° C.).

The 2-methoxy-2-oxo-3-isopropyl-1,3,2-oxazaphosphorinane is then treated in a sealed reactor with 12 parts trimethylamine and 30 parts acetonitrile for several days at 80°-90° C. The tetramethylammonium salt formed is separted by filtration to give 12.4 parts of a white hygroscopic solid.

M.Pt. = 214°-215° C.

Yield = 51%

(b) Sodium salt of $P^1$-(γ-N-isopropylammoniopropyl)phosphoric, $P^2$-cis-1-propenyl-phosphoric acid anhydride.

There is reacted overnight at 60° C. a mixture of 2.9 parts of the compound prepared under (a) above and 1.4 parts cis-1-propenylphosphonic acid in 15 parts acetonitrile. The precipitate is separated by decantation and then dissolved in a little water.

The aqueous solution is passed over a column of Amberlite resin IR 120 ($Na^+$). The water is removed in vacuo and then the residue obtained purified by chromatography on a column of activated alumina (eluant $H_2O$/MeOH: 2:1); 1.5 parts of a white hygroscopic solid are obtained.

Yield = 40%

NMR (H) $D_2O$

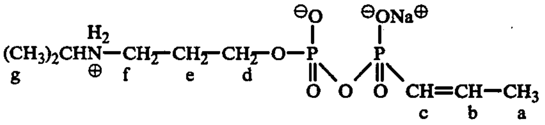

a (m) δ = 1.85 ppm b,c (m) δ between 5 and 7 ppm d (d) δ ~ 3.95 ppm e (m) δ ~ 2 ppm f (d) δ = 3.1 ppm g (d) δ = 1.12 ppm, τ = 6.66 Hz

| Analysis: $C_9H_{20}NO_6P_2Na$ | C | H | N | Na |
|---|---|---|---|---|
| Calculated | 33.4 | 6.2 | 4.33 | 7.12 |
| Found | 33.22 | 6.6 | 4.43 | 7.11 |

TLC Silica gel G (type 60)

Eluant MeOh = 80, $Et_3N$ = 5, $H_2O$ = 10

Rf = 0.63

(c) Sodium salt of $P^1$-(γ-N-isopropylammonio-propyl)-phosphoric, $P^2$-(±)-cis-1,2-epoxypropyl-phosphonic acid anhydride.

There is stirred overnight at ambient temperature 1 part of the compound obtained under (b), 2 parts of 110 volume oxygenated water, 0.02 parts sodium tungstate and 0.007 parts titriplex III; the reaction is finished as in example 8*b*. there are obtained 0.58 parts of a white solid, readily soluble in water and slightly soluble in organic solvents.

Yield = 55%

NMR (H) $D_2O$

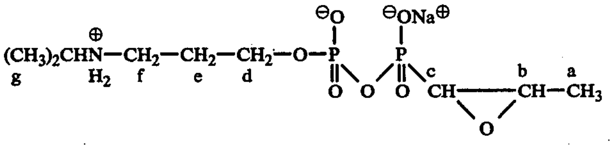

a (d) δ = 1.4 ppm, τ = 5.33 Hz b, c (m) δ ~ 3.15 ppm d (m) δ ~ 4 ppm e (m) δ ~ 1.95 ppm f (t) δ ~ 3.15 ppm g (d) δ = 1.2 ppm τ = 6.66 Hz

EXAMPLE 10

Sodium salt of $P^1$-3-methoxybutyl-phosphoric, $P^2$-(±)cis-1,2-epoxypropyl-phosphonic acid anhydride (SAB 74213)

(a) Methyl-3-methoxybutyl-phosphite.

To 68.8 parts by weight of phosphorus trichloride diluted with its own volume of methylene chloride, there is added dropwise with stirring while keeping the temperature of the reaction medium at −20° to −30° C., 52.5 parts 3-methoxybutanol diluted in its own volume of methylene chloride. The addition ended, stirring is continued for 1 hour at ambient temperature.

There is then added dropwise 64 parts methyl alcohol diluted in its own volume of methylene chloride while keeping the temperature between 0° and 5° C. The reaction ended, the solvent and gaseous products formed are removed in vacuo and the product purified by distillation.

B.Pt. $_{0.05}$ = 93° C.

(b) Methyl-3-methoxybutyl-dimethylamidophosphate.

To a solution of 18.2 parts methyl-3-methoxybutylphophite in 75 parts $CCl_4$ there is added slowly at 0°-3° C. with stirring 11 parts dimethylamine.

The addition ended, stirring is continued for 4 hours at ambient temperature, the precipitate removed by filtration, the solvent removed in vacuo and the residue then purified by distillation.

Yield = 72%

(c) Tetramethylammonium 3-methoxybutyl-dimethylamidophosphate.

There is reacted for several days at 80°-90° C. in a sealed reactor 11.25 parts of the ester obtained under b.) and 6 parts trimethylamine in 18 parts acetonitrile.The tetramethylammonium salt formed is separated by filtration after having been cooled to 0° C. 9.9 parts of a white hygroscopic solid are obtained.

M.Pt. = 210° C.
Yield = 70%

(d) Sodium salt of $P^1$-3-methoxybutylphosphoric, $P^2$-cis-1-propenyl-phosphonic acid anhydride.

There is reacted overnight at 60° C. a mixture of 8 parts of the tetramethylammonium salt obtained under (c) and 3.4 parts cis-1 propenylphosphonic acid in 20 parts acetonitrile. The precipitate is removed by filtration, the solvent evaporated off and the residue then taken up in water.

The aqueous solution is passed over a column of Amberlite resin IR 120 ($Na^+$). The water is evaporated off in vacuo and the residue then taken up in acetone; a white solid, which is separated by filtration, is obtained Yield = 72%

| Analysis: $C_8H_{16}O_7P_2Na_2$ | C | H | P | Na |
|---|---|---|---|---|
| Calculated | 28.9 | 4.81 | 18.67 | 13.85 |
| Found | 28.64 | 4.81 | 19.17 | 12.23 |

TLC Silica gel G (type 60)
Eluant: $CH_3OH$: 80, $Et_3N$: 5, $H_2O$: 10
Rf: 0.831

(e) Sodium salt of $P^1$-3-methoxybutylphosphoric, $P^2$-(±)-cis-1,2-epoxypropylphosphonic acid anhydride.

There is reacted for 3 hours at ambient temperature a mixture of 3.8 parts of the compound obtained under (d), 8.5 parts of 110 volume oxygenated water, 0.06 parts $Na_2WO_4$ and 0.02 parts titriplex III. The product formed is precipitated with acetone and separated by filtration. The product is purified by passage over a column of activated alumina using, as eluant, a mixture of water and methanol (5:1). There are obtained 2.2 parts of a white solid which is readily soluble in water.

Yield = 56%
NMR (H) $D_2O$

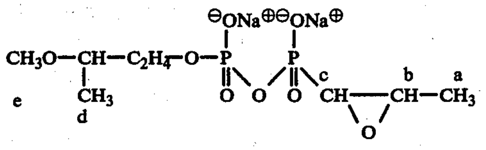

a (d) δ = 1.5 ppm, τ = 5.3 Hz
d (d) δ = 1.18 ppm, τ = 6.7 Hz
e (s) δ = 3.33 ppm
TLC Silica gel G (type 60)
Eluant: $CH_3OH$: 80, $Et_3N$: 5, $H_2O$: 5
Rf = 0.721

EXAMPLE 11

Disodium salt of $P^1$-n-propylphosphoric, $P^2$-(±) cis-1,2-epoxypropylphosphonic acid anhydride (SAB 74 208)

(a) Tetramethylammonium n-propyl-dimethylamidophosphate

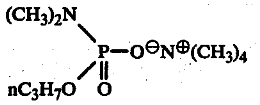

A mixture of 21.2 parts tetramethylammonium methyldimethylamidophosphate, 13 parts n-propyl bromide and 0.5 parts tribenzylamine are reacted for several days at ambient temperature with stirring. The tetramethylammonium bromide formed is removed by filtration, the solvent evaporated off in vacuo, the residue taken up in diethyl ether, filtered, then the ether is evaporated off and 10.5 parts methyl-n-propyl-dimethylamidophosphate obtained.

The 10.5 parts methyl-n-propyl-dimethylamidophosphate are reacted with 6 parts trimethylamine according to the method of Example 10c); 11.2 parts tetramethylammonium n-propyl-dimethylamidophosphate are obtained in the form of a white hygroscopic solid.

(b) Disodium salt of $P^1$-n-propylphosphoric, $P^2$-cis-1-propenylphosphonic acid anhydride. Using 4.8 parts tetramethylammonium n-propyldimethylamidophosphate, 2.44 parts of cis-1-propenylphosphonic acid and 20 parts acetonitrile and operating as in Example 7(aα), 4.05 parts (yield = 70%) of a white solid, soluble in water, are obtained.

(c) Disodium salt of $P^1$-n-propylphosphoric, $P^2$-(±)-cis-1,2-epoxypropylphosphonic acid anhydride.

There is reacted at ambient temperature for 1 hour with stirring a mixture of 3.7 parts of the compound prepared under (b) above, 6 parts of 110 volume oxygenated water, 0.06 parts $Na_2WO_4$ and 0.02 parts titriplex III.

The product formed is precipitated with acetone and separated by filtration. 3.8 parts of a white solid, which are purified by chromatography over a column of activated alumina (eluant, water/methanol 5:1), are obtained

| Analysis: $C_6H_{12}O_7Na_2P_2 \cdot H_2O$ | C | H | P | Na |
|---|---|---|---|---|
| Calculated | 23 | 4.16 | 19.82 | 14.7 |
| Found | 22.93 | 4.20 | 19.84 | 14.35 |

NMR (H) $D_2O$

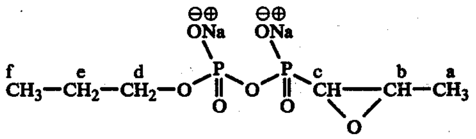

a (d) δ = 1.53 ppm, τ = 5.3 Hz
b,c (m) δ ~ 3.25 ppm
d (m) δ ~ 3.98 ppm
e (m) δ ~ 1.68 ppm
f (t) δ = 0.92 ppm

EXAMPLE 12

Disodium salt of $P^1$-ethylphosphoric, $P^2$-(±) cis-1,2-epoxypropylphosphonic acid anhydride (SAB 74 216)

(a) Tetramethylammonium ethyl-dimethylamidophosphate By replacing the 13 parts n-propyl bromide by 12 parts of ethyl bromide and operating as in Example 11 (a), tetramethylammonium ethyl-dimethylamidophosphate is obtained in the form of a white hygroscopic solid (M.Pt. 198° C.)

(b) Disodium salt of $P^1$-ethylphosphoric, $P^2$-cis-1-propenylphosphonic acid anhydride There are reacted 4.52 parts tetramethylammonium ethyl-dimethylamidophosphate and 2.44 parts cis-1 propenylphosphonic acid according to Example 11 (b); 3.7 parts (yield 68%) of a white solid are obtained.

| Analysis | C | H | P | Na |
|---|---|---|---|---|
| Calculated | 21.9 | 3.65 | 22.6 | 16.8 |
| Found | 21.33 | 3.62 | 22.44 | 17.07 |

TLC Silica gel (type 60).
Eluant: MeOH = 80, $Et_3N$ = 5, $H_2O$ = 10
Rf = 0.79

(c) Disodium salt of $P^1$-ethylphosphoric, $P^2$-(±) cis-1,2-epoxypropylphosphonic acid anhydride There are reacted 4.2 parts of the compound obtained under (b) with 10 parts of 110 volume oxygenated water according to Example 11 (c); 3.66 parts of a white solid are obtained

NMR (H) $D_2O$

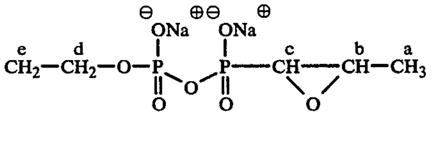

a (d) $\delta$ = 1.5 ppm, $\tau$ = 5.3 Hz
b,c (m) $\delta$ ~ 3.3 ppm
d (m) $\delta$ ~ 4.02 ppm
e (t) $\delta$ = 1.27 ppm
TLC Silica gel (type 60)
Eluant MeOH = 80, $Et_3N$ = 5, $H_2O$ = 10
Rf = 0.707

EXAMPLE 13

Disodium salt of $P^1$-(2-methoxyethyl)-phosphoric, $P^2$-(±)-cis-1,2-epoxypropylphosphonic acid anhydride (SAB 74 215)

(a) Methyl-2-methoxyethyl-phosphite

Operating as in Example 1(a) but using 38 parts 2-methoxyethanol, methyl-2-methoxyethyl-phosphite was obtained.

B. Pt.$_{0.01}$ 68°-70° C. $n_D^{20}$ 1.4215

(b) Methyl 2-methoxyethyl dimethylamidophosphate

Operating as in Example 10(b) but using the product of (a) above, methyl-2-methoxyethyl-dimethylamido-phosphate was obtained B.Pt.$_{0.01}$ 68°-70° C.
Yield = 70%

(c) Tetramethylammonium 2-methoxyethyl-dimethylamidophosphate

Operating as in Example 10(c) but using the product of (b) above, tetramethylammonium 2-methoxyethyl-dimethylamidophosphate was obtained.

M.Pt. = 218°-220° C.
Yield = 84%

(d) Sodium salt of $P^1$-(2-methoxyethyl)-phosphoric, $P^2$-cis-1-propenyl-phosphoric acid anhydride.

There are reacted 12.8 parts of the compound obtained under (c) above with 6.1 parts propenylphosphonic acid in 40 parts acetonitrile according to Example 10d); 11.5 parts of a white solid are obtained Yield = 76%
NMR (H) $D_2O$

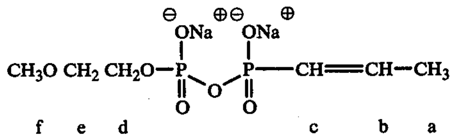

a (m) $\delta$ = 1.92 ppm
b,c (m) $\delta$ between 5.2 and 7 ppm
d(m) $\delta$ = 4.05 ppm
e (m) $\delta$ = 3.7 ppm
f (s) $\delta$ = 3.4 ppm
TLC Silica gel (type 60)
Eluant: MeOH: 80, $Et_3N$: 5, $H_2O$: 10
Rf = 0.59

(e) Sodium salt of $P^1$-(2-methoxyethyl)phosphoric, $P^2$-(±) cis-1,2-epoxypropyl-phosphonic acid anhydride.

Using 6.08 parts of the compound obtained under (d), 10 parts of 110 volume oxygenated water, 0.03 parts $Na_2WO_4$ and 0.01 parts titriplex III and operating as in Example 10(c), 5.4 parts of a white solid are obtained.

Yield = 84%
NMR (H) $D_2O$

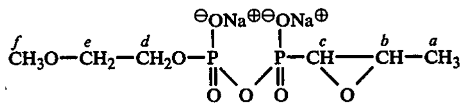

a (d) $\delta$ = 1.5 ppm, $\delta$ = 5.3 Hz
b,c (m) $\delta$ ~ 3.32 ppm
d (m) $\delta$ = 4.15 ppm
e (m) $\delta$ = 3.76 ppm
f (s) $\delta$ = 3.5 ppm
TLC Silica gel (type 60)
Eluant = MeOH: 80, $Et_3N$: 5, $H_2O$: 10
Rf = 0.694

EXAMPLE 14

Disodium salt of $P^1$-methoxycarbonylmethylphosphoric, $P^2$-(±)-cis-1,2-epoxypropylphosphonic acid anhydride (SAB 74 220)

(a) Tetramethylammonium (methoxycarbonylmethyl)-dimethyl-amidophosphate.

There is reacted for several hours at 65°-80° C. a mixture of 21.2 parts tetramethylammonium methyldimethylamidophosphate, 15.3 parts methylbromoacetate, 3 parts tribenzylamine and 100 parts acetonitrile.

After having removed the solvent, the residue is taken up in chloroform and the chloroform solution washed with an aqueous solution of sodium bicarbonate. The chloroform solution is dried and evaporated and the residue obtained is treated with 7 parts trimethylamine according to Example 10(c).

(b) Disodium salt of $P^1$-methoxycarbonylmethylphosphoric, $P^2$-cis-1,2-propenylphosphonic acid anhydride.

There is reacted for 2 days at 70° C. a mixture of 2.7 parts of compound (a) prepared above, 1.22 parts cis-1-propenylphosphonic acid and 10 parts acetonitrile and the preparation is completed according to Example 7(a) to give 2.6 parts of a white solid.

Yield = 70%

(c) Disodium salt of $P^1$-methoxycarbonylmethylphosphoric, $P^2$-(±) cis-1,2-epoxypropylphosphonic acid anhydride.

There is stirred for an hour at ambient temperature a mixture of 2.6 parts of the compound prepared under (b), 5 ml of 110 volume oxygenated water, 0.03 parts $Na_2WO_4$ and 0.01 parts titriplex III, and the operation then completed according to Example 7(b). 1.1 parts of a white solid are obtained.

NMR (H) $D_2O$

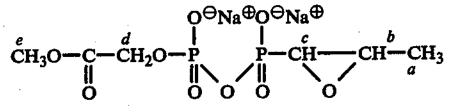

a (d) $\delta$ = 1.5 ppm J = 5.3 hz
b, c (m) $\delta \sim$ 3.3 ppm
d (d) $\delta$ = 4.7 ppm
J = 9.3 Hz
e (s) $\delta$ = 3.9 ppm.

EXAMPLE 15

Sodium salt of $P^1$-(3-trimethylammoniopropyl)phosphoric $P^2$-(±) cis-1,2-epoxypropylphosphonic acid anhydride (SAB 75 222).

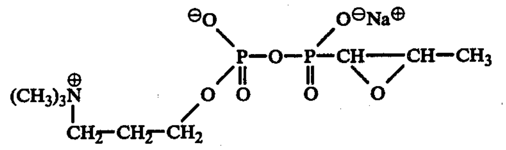

(a) Morpholine salt of $P^1$-(3-trimethylammoniopropyl) phosphoric, $P^2$-cis-]-propenylphosphonic acid anhydride.

There is stirred overnight at 70° C. a mixture of 5.32 parts morpholino-phosphorylhomocholine prepared according to French Patent No. 72.43 780 of Dec. 8, 1972, 2.44 parts cis-1-propenylphosphonic acid and 20 parts acetonitrile. The product is separated by filtration and 6.25 parts of a white hygroscopic solid are obtained.

Yield = 81%

(b) Sodium salt of $P^1$-(3-trimethylammoniopropyl)phosphoric $P^2$-(±) cis-1,2-epoxypropylphosphonic acid anhydride.

To a solution of 3 parts of the compound prepared under (a) above, 0.1 part of [W $(O_2)_2O$]. HHPT. $H_2O$ in 6 parts methanol, there are added slowly at ambient temperature 0.5 parts of 85% oxygenated water. After the addition, the reaction mixture is left overnight at ambient temperature and then there is added 0.56 parts alcoholic sodium hydroxide solution and the product precipitated by the addition of acetone. After purification by chromatography on a column of activated alumina (eluant, water/methanol - 4:1) 1.7 parts of a white solid are obtained.

Yield: 65%

EXAMPLE 16

Disodium salt of P-L-(B-cyanoethyl) phosphonic, p-2 (±) -cis- epoxy-1,2propylphosphoric anhydride.

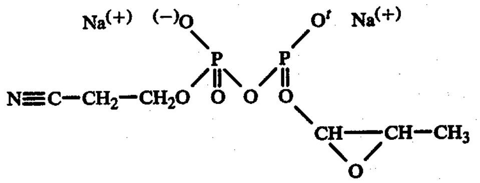

(a) dimethylamino-2 oxo-2 dioxaphospholanne - 1,3,2.

Using a solution of 5 parts of dimethylamine and 10 parts of trimethylamine in 180 parts of benzene; and slowly to this solution at 0° C., a solution of 13.85 parts of chloro-2 oxo-2 dioxaphospholanne-1,3,2 in 27 parts of benzene.

When addition is finished, the mixture is agitated at room temperature then the hydrochloride is eliminated by filtration then the solvant is evaporated under vacuum. The product obtained is added to cyclohexane, then the product is isolated by filtration.

M.P. C. about 50° C., yield 80%

(b) N,N-dimethylamidophosphate at ( B-cyanoethyl) and of Na. 14.2 parts of dimethylamino-2 oxo-2 dioxaphospholanne-1,3,2 and 4.9 parts of Na CN in 70 parts of DMF are mixed at room temperature for several days.

The product obtained is filtered, then small amounts of Na CN are withdrawn by dissolving the solid in anhydrous methanol then the pH of the mixture is adjusted at 8.8 with a weak acid resin; after filtration a white solid is obtained which is soluble in isopropanol, DMSO, DMF.

($c_1$) Sodium and dimethylammonium salt of P-L(B-cyanoethyl)-phosphoric, p2-cis-propenyl-1 phosphonic acid: 13.5 parts of (B-cyanoethyl) and Na N,N-dimethylamido phosphate and 8.1 parts of cis-propenyl-1 phosphonic acid are mixed for 4 hrs at 70° C. in 40 parts of acetonitrile.

After filtration, 10 parts of white solid are obtained; the NMR (H) spectrum of which shows that this compound is a mixture of disodium salt and sodium dimethylammonium salt.

The product is purified by passing through a silicious column (eluant : MeOH : 80, $Et_3N$ : 5, $H_2O$ = 15). After evaporation of solvants one obtains 8.2 parts of a mixture of bis-dimethylammonium salt and Nadimethylammonium salt.

($c_2$) disodium salt of P-L-(B-cyanoethyl) phosphoric, $P_2$-cis-propenyl-1 phosphonic anhydride is quantitatively obtained by passing the mixture of mixed salts through an Amberlite IR 120 ($Na^+$) resine column.

(d) One slowly adds, at room temperature, with stirring, 0.25 parts of oxygenated water at 85% to a mixture of 2 parts of disodium salt of P-L-(B-cyanoethyl) phosphoric, p-2-cis-propenyl-1 phosphonic anhydride and 0.06 parts of $Na_2W_2O_4$ in 4.5 parts of methanol.

The mixture is stirred for one night at room temperature and the product is precipitated by addition of acetone.

Yield 95%

| Analysis : $C_6H_9NO_7P_2Na_2$ , 0,5 $H_2O$ | C | H | N | P |
|---|---|---|---|---|
| calculated | 22,2 | 3,01 | 4,33 | 19,19 |
| Found | 21,7 | 3,01 | 4,27 | 18,93 |

EXAMPLE 17

Disodium salt of P-L methylphosphoric $p_2$-(±)-cis-epoxy-1,2-polyphosphonic anhydride (SAB 76 227).

One adds, for 3 hrs. at 70° C., with stirring, 2.59 parts of (+)-cis-epoxy-1,2 propylphosphonate of (−)-phenyl-1 ethylammonium and 2.59 parts of dimethylamidophosphate of methyl and tetramethylammonium and 2.29 parts of picric acid in 25 parts of p,α-dimethylbenzylalcool.

The precipitate is eliminated by filtration and the valuable product is extracted with water; after washing the aqueous phase with chloroform and ether and after passing this phase on Amberlite IR 120 ($Na^+$) column and after drying, the product is treated by hot methanol. The final product is a white solid having an $[\alpha]_{405}^{20}$ + 2. ($\epsilon = S_1H_2O$ )

Tests have shown that cis-1,2 epoxypropylphosphonic acid derivatives have antibiotic and antibilharziasis properties.

Bilharzia or schistosomosis is the second most widespread serious disease in the world. It is caused by certain trematodes, the schistosomes. There is a distinction between intestinal bilharzia, caused by *Schistosoma mansoni,* aretrio-venous bilharzia, caused by *S. japonicum,* and urogenital bilharzia, caused by *S. haematobium.*

A halt in the progress of the disease can be achieved by curative treatment of the sufferers by use of drugs, by breaking the epidemiological cycle at the stage of the penetration by the cercariae analogously with the protection obtained by use of chloroquine against malaria.

In the treatment of bilharzia, dehydroemetine, organo-antimony derivatives, thioxanthone derivatives and, above all, niridazole (Ambilhar R), derived from nitrothiazole, have been used.

It has been essentially a case of a therapeutic curative, the drugs only acting on the adult forms and not on the larval infecting forms, the schistosomules.

On the other hand, these known drugs and, in particular, the nitrothiazole derivatives frequently cause digestive disturbances and sometimes lead to neurological problems accompanied by, for example, acute psychiatric symptoms or epileptic fits. These side-effects have necessitated and surveillance throughout the course of the treatment and have even lead to the therapy having to be ceased.

It is thus of great importance to provide an active drug for oral administrative which has the two advantages of:

(a) acting on the schistosomule stage with the object of interrupting the parasitic development cycle in man and as a consequence obtaining the eradication of the disease (mass suppressive prophylaxis);

(b) also having as low a toxicity as possible to permit prophylactic campaigns which do not require constant medical surveillance.

The compounds of the invention fulfil these two conditions.

TOXICITY

The derivatives of the invention have an extremely low toxicity. As an example the toxicities (lethal dose 50 or LD 50) determined by the method of Karber and Behrens (Arch. Exp. Pathol. Pharm. 177 1935, page 379) in Evic Ceba ♀ Swiss EOPS NMRI Han mice of 24–26 g, for several compounds are given below.

TABLE 1

| | DL 50 oral | in g/kg intravenous |
|---|---|---|
| S A B 73 196 | 17 | 0,68 |
| S A B 74 200 | >10 | 0,55 |
| S A B 74 202 | 15 | 1,5 |
| S A B 74 207 | 14,5 | 1,4 |
| S A B 74 212 | >10 | 2,9 |

ANTIBACTERIAL ACTIVITY

The compounds of the invention have an in vivo antibacterial activity both on gram positive and on gram negative bacteria.

As an example we described the activity of several SAB products on infected mice.

Activity on Salmonella typhimurium (strain C5)

Batches of 15 mice C 3 H "pathogen free" and weighing 20 g received intraperitoneally $2.10^4$ bacteria in 0.20 ml of physiological serum and simultaneously orally 0.5 mm test compound in 0.25 ml distilled water. The treatment lasted for 5 days i.e. in total 2.5 mg test compound per mouse.

The results of the test are evaluated at 15 days (Table II)

TABLE II

| | Number of mice surviving at 15 days | Average survival time (in days) of mice dead before 15 days |
|---|---|---|
| SAB 7 316 | 10 | 6,2 |
| SAB 74 200 | 15 | |
| SAB 74 202 | 14 | 8 |
| SAB 74 212 | 15 | |
| Control | 0 | 10 |

Investigation for bacteria in the blood and in the cells of the surviving mice was negative.

Activity on Staphylococcus aureus (strain 124)

Lots of 10 mice received intraperitoneally $10^8$ bacteria in suspension in 0.20 ml of sterile 5% mucin.

The previous day the mice in the batch to be treated has received orally 2 mg of the test compound in 0.25 ml distilled water.

The treatment is repeated on the day of microbial inoculation and then for 3 days, i.e. 5 days in all, each mouse thus receiving 10 mg of test compound.

The results of the test are evaluated at 15 days (Table III)

TABLE III

| | Number of mice surviving at 15 days | Average survival (in days) of the mice dead before 15 days |
|---|---|---|
| SAB 7 316 | 10 | 6,2 |
| SAB 74 200 | 7 | |
| SAB 74 202 | 10 | |
| SAB 74 212 | 10 | |
| Control | 2 | 2,5 |

Activity on Escherichia coli (strain from wild rodent)

Batches of 10 mice received intraperitoneally $10^8$ bacteria in suspension in 0.20 ml sterile 5% mucin.

The previous day the mice in the batch to be treated had received orally 2 mg test compound in 0.25 ml distilled water.

The treatment was repeated on the day of microbial inoculation and then for 3 days, i.e. in total 5 days, each mouse thus receiving 10 mg of compound.

The results of the test are evaluated at 15 days. (Table IV)

TABLE IV

| | Number of mice surviving at 15 days | Average survival (in days) of mice dead before 15 days |
|---|---|---|
| SAB 7 316 | 8 | 5,5 |
| SAB 74 200 | 10 | |
| SAB 74 202 | 9 | 5 |
| SAB 74 212 | 10 | |
| Control | 3 | 3,2 |

ANTIBILHARZIASIS ACTIVITY

The experiment consists in infecting mice with cercariae of Schistosoma mansoni and treating them immediately orally with the test compound, the total length of treatment being 5 days.

The experimental conditions followed are in accord with the works of:

WARREN K. S. and PETERS P. A.: Comparison of penetration and maturation of Schistosoma mansoni in the hamster, mouse, guinea pig and rat. Amer. J. Trop. Med. Hyg. 1967, 16, 718–722.

SMITH S. R. and TERRY R. J.: The infection of laboratory hosts with cercariae of S. mansoni and the recovery of adult worms, Parasitology, 1965, 55, 695–700.

STIREWALT M. A., KUNTZ R. E. and EVANS A. S.: The relative susceptibilities of commonly used laboratory mammals to infection by S. mansoni, Amer. J. Trop. Med. Hyg. 1966, 31, 57 2.

The strain of S. mansoni was isolated in Madagascar in 1966, imported into France in 1968 and refined by successive passage through hamsters (45 days) and the mollusc vector Biomphalaria pfeifferi (at 23° C., cercariae emission in 45 days).

The cercariae were washed and counted after their emission.

The mice were infested subcutaneously by injecting under the skin of the flank 100 cercariae in 0.25 ml water per mouse. The mice were infested at a rate of 20 per batch as well as 20 mice of a control lot.

The test compound was administered orally to the mice by means of a stomach tube immediately after their infestation.

The administered doses were 2 mg test compound per mouse per day for 5 days i.e. a total of 10 mg per mouse.

All the mice were killed on the 45th day.

The peritonea and the livers are washed according to the technique of Smith and the adult male and female schistosomes counted.

Anatomo-pathological examination of the liver, of the spleen and of the intestine of the mice was carried out.

In these conditions there were found among the control mice, on washing the liver and the peritonea, between 40 and 60 adult schistosomes per 100 cercariae injected.

As an example the results obtained in the mice treated are set out below: (Tables V, VI, VII, VIII).

TABLE V

The results of the tests of activity of SAB 7319 at a rate of 1 mg per day for 5 days in mice infested with *S. mansoni.*

| | Number of worms in the control mice ♂ | ♀ | Number of worms in the treated mice ♂ | ♀ |
|---|---|---|---|---|
| Liver | 8 | 4 | 0 | 1 |
| Intestine | 19 | 9 | 7 | 2 |
| Total | 27 | 13 | 7 | 3 |

TABLE VI

The results of the tests of activity of SAB 74 208 at a rate of 2 mg a day for 5 days in mice infested with *S. mansoni.*

| | Number of worms in the control mice ♂ | ♀ | Number of worms in the treated mice ♂ | ♀ |
|---|---|---|---|---|
| Liver | 15 | 6 | 4 | 1 |
| Intestine | 22 | 12 | 7 | 3 |
| Total | 37 | 18 | 11 | 4 |

TABLE VII

The results of the tests of activity of SAB 74210 at a rate of 2 mg per day for 5 days in mice infested.

| | Number of worms in the control mice ♂ | ♀ | Number of worms in the treated mice ♂ | ♀ |
|---|---|---|---|---|
| Liver | 15 | 6 | 13 | 5 |
| Intestine | 22 | 12 | 23 | 3 |
| Total | 37 | 18 | 36 | 8 |

TABLE VIII

Results of the tests of activity of SAB 74212 at a rate of 2 mg per day for 5 days in mice infested with *S. mansoni.*

| | Number of worms in the control mice ♂ | ♀ | Number of worms in the treated mice ♂ | ♀ |
|---|---|---|---|---|
| Liver | 15 | 6 | 5 | 2 |
| Intestine | 22 | 12 | 12 | 5 |

-continued

| | Number of worms in the control mice | | Number of worms in the treated mice | |
|---|---|---|---|---|
| | ♂ | ♀ | ♂ | ♀ |
| Total | 37 | 18 | 17 | 7 |

TABLE IX

Results of the tests of activity of SAB 76 227 dextrorotatory enantiomer at the rate of 1 mg a day for 5 days in mice infested with *S. mansoni.*

| | Numbers of worms in the control mice | | Number of worms in the treated mice | |
|---|---|---|---|---|
| | ♂ | ♀ | ♂ | ♀ |
| Liver | 9 | 4 | 0 | 0 |
| Intestine | 50 | 25 | 5 | 0 |
| Total | 59 | 29 | 5 | 0 |

Three other tests have been carried out administering orally to the mice a single dose of SAB 73 196, either 1.25 mg or 2.5 mg or 5 mg.

Even if these tests do not give evidence of a dose-action relationship, they demonstrate two remarkable facts:

a very significant reduction in the number of Female worms the single dose activity, the importance of which is considerable in prophylactic treatment.

TABLE X

Results of the tests of activity of SAB 73 196 administered as a single dose to mice infested with *S. mansoni.*

| Number of worms in the control mice | | | Numbers of worms in the mice treated with a single dose | |
|---|---|---|---|---|
| 0 | 0 | Dose in mg | 0 | 0 |
| 14 | 26 | 1.25 | 5 | 2 |
| 14 | 26 | 2.50 | 3 | 1 |
| 14 | 26 | 5 | 11 | 3 |

A considerable reduction in the number of adult schistosomes in the treated mice is observed.

An anatomo-pathological examination of the mice gave the following results:

spleen: spleen enlargement in the control mice, absence of spleen enlargement in the treated mice;

intestine: inflammatory granulomae centred on eggs in the control mice, no eggs in the treated mice;

liver: inflammatory granulomae with eggs in the control mice, no eggs in the treated mice.

It is extremely important to note the absence of eggs in the mice treated with SAB 73196.

Finally, phenomena of toxicity have never been observed in the treated mice.

The preventative activity against bilharziasis of the racemic derivatives clearly appears as coming from the dextrorotatory enantiomer which is contained in these derivatives.

In addition, it has been discovered that the dextrorotatory cis-epoxy-1,2-propyl-phosphonic acid, its salts and derivatives present excellent anti-bilharziosis properties, whilst the laevorotatory enantiomer does not have any at the doses employed.

The results obtained in the mice treated with the sodium salt of (+)-cis-epoxy-1,2-propyl-phosphonic acid are reported hereinbelow (Table XI hereinafter) and, comparatively, the results recorded with its laevorotatory isomer, the sodium salt of (−)-cis-epoxy-1,2-propyl-phosphonic acid (fosfomycine) (Table XII hereinbelow).

TABLE XI (+)-cis-epoxy-1,2-propylphosphonic acid (sodium salt)

Results of the tests of activity by the oral route at a dose of 2 mg per day for 5 days in the mouse infested with *S. mansoni.*

| | Number of worms in the control mice | | Number of worms in the treated mice | |
|---|---|---|---|---|
| | ♂ | ♀ | ♂ | ♀ |
| Liver | 8 | 2 | 0 | 0 |
| Intestine | 27 | 12 | 7 | 5 |
| Total | 35 | 14 | 7 | 5 |

An anatomo-pathological examination of the organs gives:

Spleen: Spleen enlargement in the control mice, absence of spleen enlargement in the treated mice;

Intestine: Inflammatory granulomae centred on eggs in the control mice, no eggs in the treated mice;

Liver: Inflammatory granulomae with eggs in the control mice, no eggs in the treated mice.

Moreover, no phenomenon of toxicity has ever been observed in the treated mice.

TABLE XII (−)-cis-epoxy-1,2-propylphosphonic acid (sodium salt) (fosfomycine)

Results of the tests of activity by the oral route at a dose of 2 mg per day for 5 days in the mouse infested with *S. mansoni.*

| | Number of worms in control mice | | Number of worms in the treated mice | |
|---|---|---|---|---|
| | ♂ | ♀ | ♂ | ♀ |
| Liver | 8 | 2 | 11 | 5 |
| Intestine | 27 | 12 | 27 | 17 |
| Total | 35 | 14 | 38 | 22 |

After an anatomo-pathological examination of the organs, numerous inflammatory granulomae centred on eggs are observed, both in the liver and in the intestines of the treated animals.

These two parallel tests show that:

the laevorotatory isomer of the cis-epoxy-1,2-propylphosphonic acid (sodium salt) or fosfomycine is totally inactive and does not inhibit either the cycle of development of the schistosomules into adult worms, nor the laying of eggs;

the dextrorotatory isomer of the cis-epoxy-1,2-propyl-phosphonic acid (sodium salt) is very active since it totally inhibits the laying of eggs and since there is a very considerable reduction in the number of adult worms, both males and females.

CONCLUSIONS

The derivatives of the invention administered by the oral route in the mouse infested with cercariae of *S. mansoni* have the property of reducing the development of the adult schistosomes and, more particularly, the female forms, even at single dose.

Concomittantly, an anatomo-pathological examination shows a total or quasi-total absence of eggs in the treated mice.

Moreover, the tolerance to the treatment is excellent.

The dextrorotatory isomer of the cis-epoxy-1,2-propylphosphonic acid has an effect which is totally similar.

In this way, the conditions necessary for a prophylactic approach to the disease and for mass treatment are combined.

Antibiotic activity complementary to the antibilharziasis activity of the derivatives in their racemic form is interesting due to the frequent microbial superinfections suffered by the people inhabiting infested tropical zones.

CURATIVE ANTIBILHARZIASIS ACTIVITY AT THE ADULT STAGE

The tests carried out have enabled the following facts to be demonstrated:

the derivatives of the invention in their racemic form have only a slight curative activity in the mouse infested with cercariae of *S. mansoni*, the association of these racemic derivatives of an amine such as benzylamine or methylbenzylamine brings out the curative activity, the dextrorotatory enantiomers of these derivatives are curatively active without it being necessary to add an amine thereto.

Curative activity of the racemic SAB 73196 in the presence of benzylamine hydrochloride The experiment consists in infecting mice by the transcutaneous route with 100 cercariae of *S. mansoni* and in treating them for 5 days by the oral route with the products to be tested from the 40th day following the infestation.

The daily doses employed were 1 mg of SAB 73196 and 0.5 mg of benzylamine hydrochloride.

An examination of the mice was carried out either immediately at the end of the treatment or after a supplementary period of 10 days.

The results obtained on batches of 25 mice, of which 10 were sacrificed on the 45th day and 15 on the 55th day after the infestation are shown hereinbelow (Table XIII).

TABLE XIII

Curative effects obtained by administering for 5 days the association of 1 mg of SAB 73196 and of 0.5 mg of benzyl amine hydrochloride.
(infestation by 100 cercariae)

| | Number of worms in control mice | | | | Number of worms in the treated mice | | | |
|---|---|---|---|---|---|---|---|---|
| | at 45 days 10 mice | | at 55 days 15 mice | | at 45 days 10 mice | | at 55 days 14 mice (see note) | |
| | ♂ | ♀ | ♂ | ♀ | ♂ | ♀ | ♂ | ♀ |
| Liver | 5 | 4 | 5 | 3 | 1 | 0 | 0 | 0 |
| Intestine | 17 | 7 | 20 | 12 | 5 | 3 | 0 | 0 |
| Total | 22 | 11 | 25 | 15 | 6 | 3 | 0 | 0 |

Note: the 15th mouse has 10 worms♂ and 2 worms ♀in the intestine

An anatomo-pathological examination therefore reveals that, on the 55th day, i.e. 10 days after the stopping of the treatment, all the worms are dead in 14 mice out of 15.

The association of the SAB 73196 and the benzylamine hydrochloride has a very high curative activity vis-a-vis the infestation by *S. mansoni*.

In another experiment, the infestation of the mice was effected by a massive quantity of cercariae (1000 by the transcutaneous route). The treatment of 5 days was started on the 48th day of the infestation and the anatomo-pathological examination was carried out on the 61st day, i.e. 8 days after the end of the treatment.

The results of this treatment are given in Table XIV hereinbelow.

TABLE XIV

Curative effects obtained by administrating for 5 days the association of 1 mg of SAB 73196 and of 0.5 mg of benzylamine hydrochloride.
(infestation by 1000 cercaria)

| | Number of worms in control mice (on 48th day) | | Number of worms in treated mice (on 61st day) | |
|---|---|---|---|---|
| | ♂ | ♀ | ♂ | ♀ |
| Liver | 160 | 80 | 49 | 24 |
| Intestine | 44 | 35 | 2 | 1 |
| Total | 204 | 115 | 51 | 25 |

The examination revealed that 99% of the worms counted in the treated mice are dead.

Curative activity of the SAB 76227, dextrorotatory enantiomer of the disodium salt of p1-methylphosphoric p2-cis-epoxy-1,2-propylphosphonic anhydride (SAB 74207)

The SAB 76227 was administered at a dose of 1 mg for 5 days from the 45th day of the infestation.

An anatomo-pathological examination was carried out at the end of the treatment and 10 days after the end of the treatment, i.e. on the 50th and 60th days.

The results are shown in Table XV hereinbelow.

TABLE XV

Curative effects obtained by administering during 5 days 1 mg of SAB 76227 (infestation by 100 cercariae)

| | Number of worms in control mice (at 45th day) | | Number of worms in treated mice (at 50th day) | |
|---|---|---|---|---|
| | ♂ | ♀ | ♂ | ♀ |
| Liver | 8 | 3 | 2 | 1 |
| Intestine | 34 | 15 | 0 | 0 |
| Total | 42 | 18 | 2 | 1 |

An examination reveals that at the 50th day the worms counted are living but that on the 60th day, all the worms are dead.

Curative activity of the dextrorotatory cis-epoxy-1,2 propylphosphonic acid

The dextrorotation enantiomer of the cis-epoxy-1,2-propylphosphonic acid, its salts and derivatives also possess a very intense curative activity on the bisharziosis which the laevorotatory isomer does not prevent.

One of the results obtained is presented hereinbelow.

TABLE XVI

Curative effects obtained by administering for 5 days 1 mg of sodium salt of (+)-cis-epoxy-1,2 propylphosphonic acid (infestation by 100 cercariae)

| | Number of worms in control mice (at 55th day) | | Number of worms in treated mice (at 55th day) | |
|---|---|---|---|---|
| | ♂ | ♀ | ♂ | ♀ |
| Liver | 5 | 3 | 0 | 0 |
| Intestine | 20 | 12 | 1 | 0 |
| Total | 25 | 15 | 1 | 0 |

An anatomo-pathological examination shows that on the 55th day i.e. 10 days after the stopping of the treatment, all the worms except one are dead.

The livers are rich in inflammatory granulomae centred on egges, this proving that the females have laid eggs and have disappeared under the effect of the treatment.

CONCLUSION

The derivatives of the invention administered by the oral route from the 40th day of the infestation of the mouse by the cercariae of *S. mansoni* have the property of lysing the adult worms.

This curative action necessitates the addition of an amine such as the benzylamine in the case of the derivatives in their racemic form. The dextrorotatory enantiomers are active directly.

It thus appears that the curative and preventative antibilharziasis activities must be related to the dextrorotatory enantiomers of the derivatives of the invention.

Pharmaceutical compositions

These new phosphorylated derivatives may be administered in oral or parenteral pharmaceutical forms.

For administration by the oral route, the derivatives will preferably used in the form of calcium salts, but for the parenteral route (I.M. or I.V. routes), the sodium salts will be recommended.

The posology in the adult is from 1 to 3 g per 24 hours by the oral route to be distributed throughout the day (in the form of tablets, gelatine capsules, suspensions, granules, etc.).

Long-acting compositions (called "delayed action" forms) enable the administration to be reduced to one or twice daily.

The following example, given by way of non-limiting example, illustrates a composition according to the invention.

EXAMPLE

Tablets are prepared in accordance with the usual technique with the following composition:

| | |
|---|---|
| - calcium salt of p1-methyl phosphoric p2-cis-epoxy-1,2-propyl-phosphonic anhydride (SAB 73196) | 400 mg |
| - benzylamine hydrochloride | 200 mg |
| - colloidal silica | 10 mg |
| - talc | 50 mg |
| - starch | 40 mg |

What is claimed is:

1. A method for treating bilharziasis comprising administering to a patient in need of said treatment an effective amount for treating bilharziasis of dextrorotatory cis-epoxy-1,2 propylphosphonic acid or a pharmaceutically acceptable salt thereof.

2. The method of claim 1, wherein dextrorotatory cis-epoxy-1,2 propylphosphonic acid sodium salt is administered orally.

3. A method of treating incipient bilharziasis in a patient in need of said treatment which comprises administering to the patient an effective amount of dextrorotatory cis-epoxy-1,2 propylphosphonic acid or a pharmaceutically acceptable salt thereof to act on the schistosomule stage of bilharzias.

4. The method of claim 3, wherein dextrorotatory cis-epoxy-1,2 propylphosphonic acid is administered orally to the patient.

* * * * *